(12) United States Patent
Tanaka et al.

(10) Patent No.: US 9,475,755 B2
(45) Date of Patent: *Oct. 25, 2016

(54) PROPHYLACTIC AGENT FOR CHRONIC KIDNEY DISEASE

(71) Applicant: SBI Pharmaceuticals Co., Ltd., Tokyo (JP)

(72) Inventors: Tohru Tanaka, Tokyo (JP); Motowo Nakajima, Tokyo (JP); Fuminori Abe, Tokyo (JP); Satofumi Kawata, Tokyo (JP); Takeo Kohda, Tokyo (JP)

(73) Assignee: SBI Pharmaceuticals Co., Ltd, Tokyo (JP)

( * ) Notice: Subject to any disclaimer, the term of this patent is extended or adjusted under 35 U.S.C. 154(b) by 53 days.

This patent is subject to a terminal disclaimer.

(21) Appl. No.: 14/350,526

(22) PCT Filed: Oct. 5, 2012

(86) PCT No.: PCT/JP2012/075997
§ 371 (c)(1),
(2) Date: Apr. 8, 2014

(87) PCT Pub. No.: WO2013/054765
PCT Pub. Date: Apr. 18, 2013

(65) Prior Publication Data
US 2014/0256806 A1    Sep. 11, 2014

(30) Foreign Application Priority Data

Oct. 12, 2011  (JP) ................................ 2011-225382
Mar. 30, 2012  (JP) ................................ 2012-081150

(51) Int. Cl.
| A61K 31/195 | (2006.01) |
| A01N 37/44 | (2006.01) |
| A01N 37/12 | (2006.01) |
| C07C 229/22 | (2006.01) |
| A61K 31/197 | (2006.01) |
| A61K 31/28 | (2006.01) |
| A61K 33/24 | (2006.01) |
| A61K 33/26 | (2006.01) |
| A61K 33/28 | (2006.01) |
| A61K 33/30 | (2006.01) |
| A61K 33/34 | (2006.01) |
| A61K 31/295 | (2006.01) |
| C07F 15/02 | (2006.01) |
| A61K 31/215 | (2006.01) |

(52) U.S. Cl.
CPC .......... C07C 229/22 (2013.01); A61K 31/197 (2013.01); A61K 31/215 (2013.01); A61K 31/28 (2013.01); A61K 31/295 (2013.01); A61K 33/24 (2013.01); A61K 33/26 (2013.01); A61K 33/28 (2013.01); A61K 33/30 (2013.01); A61K 33/34 (2013.01); C07F 15/02 (2013.01)

(58) Field of Classification Search
CPC .......... A61K 2300/00; A61K 31/197; A61K 31/215; A61K 31/295; A61K 33/24; A61K 33/26; A61K 33/30; A61K 33/34; A61K 31/28
USPC ............. 514/502; 562/567; 556/42, 57, 110, 556/118, 138
See application file for complete search history.

(56) References Cited

U.S. PATENT DOCUMENTS

| 9,018,257 | B2* | 4/2015 | Rephaeli ............ A61K 41/0061 514/547 |
| 9,095,165 | B2* | 8/2015 | Tanaka ...................... A23L 1/30 |
| 2004/0234555 | A1 | 11/2004 | Oshida et al. |
| 2005/0020487 | A1* | 1/2005 | Klaus ..................... A61K 31/00 514/183 |
| 2008/0026075 | A1 | 1/2008 | Kondo et al. |
| 2008/0287368 | A1 | 11/2008 | Yu et al. |
| 2009/0227665 | A1 | 9/2009 | Zicker et al. |
| 2011/0196033 | A1 | 8/2011 | Tanaka |
| 2015/0290159 | A1* | 10/2015 | Tanaka ...................... A23L 1/30 514/502 |

FOREIGN PATENT DOCUMENTS

| CN | 1538839 A | 10/2004 |
| CN | 102164596 A | 8/2011 |
| EP | 1785132 A1 | 5/2007 |
| EP | 2340821 A1 | 7/2011 |
| JP | 2006-008720 A | 1/2006 |
| JP | 2006-069963 A | 3/2006 |
| JP | 2008-536935 A | 9/2008 |
| JP | 2009-504766 A | 2/2009 |

(Continued)

OTHER PUBLICATIONS

Berkovitch-Luria et al., "A multifunctional 5-aminolevulinic acid derivative induces erythroid differentiation of K562 human erythroleukemic cells", Available online Jun. 13, 2012, European Journal of Pharmaceutical Sciences, 47(1), pp. 1-294.*

(Continued)

Primary Examiner — My-Chau T Tran
(74) Attorney, Agent, or Firm — Osha Liang LLP

(57) ABSTRACT

A method for ameliorating and/or preventing chronic kidney disease includes administering to a subject in need thereof an agent containing 5-aminolevulinic acid (ALA) or a derivative thereof, or a salt thereof as an active ingredient. Preferably, these ALAs contain a metal-containing compound, such as sodium ferrous citrate. The above-mentioned ALAs, ALA; various esters, such as ALA methylester, ALA ethylester, ALA propylester, ALA butylester, and ALA pentylester; and hydrochlorides, phosphates, and sulfates, and the like of these ALA esters are preferred examples.

10 Claims, 1 Drawing Sheet

(56) References Cited

FOREIGN PATENT DOCUMENTS

| JP | 2011-016753 A | 1/2011 |
|---|---|---|
| JP | 4754731 B2 | 8/2011 |
| WO | 2008/005217 A2 | 1/2008 |
| WO | 2010/050179 A1 | 5/2010 |

OTHER PUBLICATIONS

EPO Communication with Extended European Search Report dated Apr. 10, 2015, issued by the European Patent Office in corresponding European Patent Application No. EP-12839430.1 (6 pages).

First Office Action issued Feb. 25, 2015, by the State Intellectual Property Office of the People's Republic of China in corresponding Chinese Patent Application No. CN 201280060370.3, with English translation (13 pages).

International Search Report mailed Dec. 11, 2012, in corresponding International Application No. PCT/JP2012/075997, with English translation (6 pages).

Ienaga, Kazuharu, et al., "First Indications Demonstrating the Preventive Effects of NZ-419, a Novel Intrinsic Antioxidant, on the Initiation and/or Progression of Chronic Renal Failure in Rats"; Biol. Pharma. Bull., vol. 32, No. 7, 2009; pp. 1204-1208.

* cited by examiner

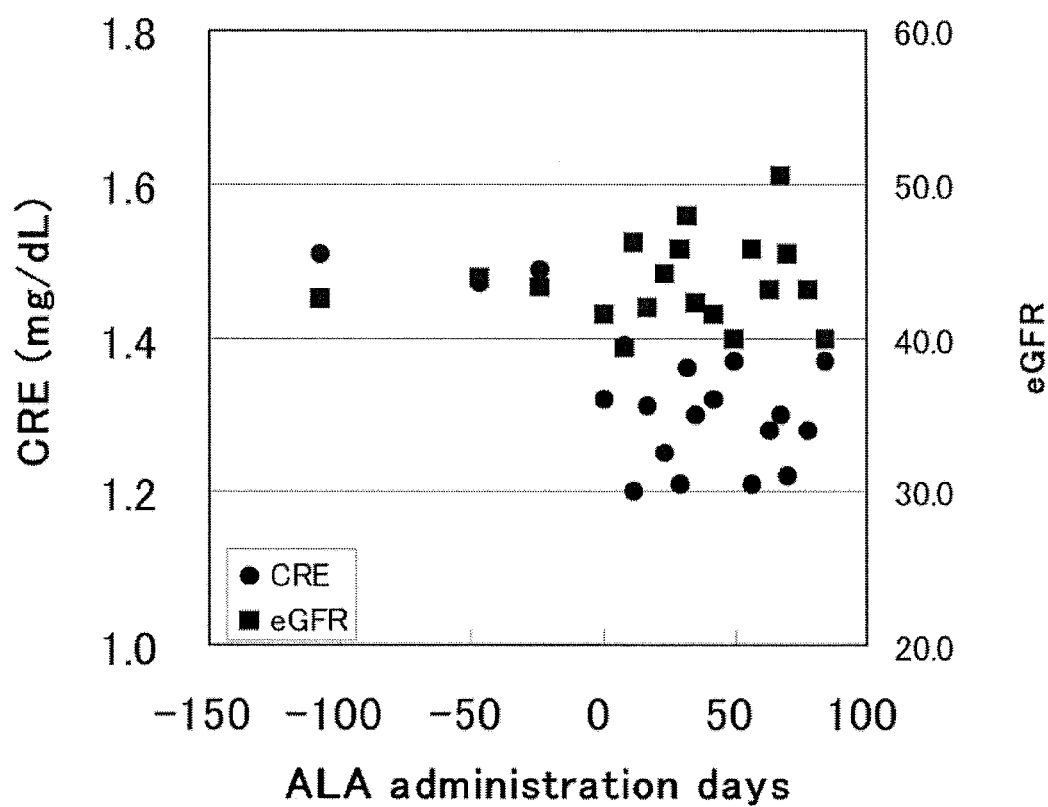

PROPHYLACTIC AGENT FOR CHRONIC KIDNEY DISEASE

CROSS REFERENCE TO RELATED APPLICATIONS

This is a national stage application based on PCT/JP2012/075997, filed on Oct. 5, 2012, which claims priority to Japanese Patent Application Nos. 2011-225382, filed on Oct. 12, 2011, and 2012-081150, filed on Mar. 30, 2012. This application claims the priority of these prior applications and incorporates their disclosures by reference in their entireties.

TECHNICAL FIELD

The present invention relates to an agent for ameliorating and/or preventing chronic kidney disease, and more specifically, relates to an agent for ameliorating and/or preventing chronic kidney disease comprising 5-aminolevulinic acid (ALA) or a derivative thereof, or a salt thereof.

BACKGROUND ART

Chronic kidney disease indicates a disease in which there is chronic deterioration of renal function, and even if the same kidney disorder, is differentiated from acute nephritis and the like. Since the kidneys fulfill the role of removing by filtration waste products in blood, waste products buildup in the body when renal function deteriorates, leading to the showing of so-called uremic symptoms. Also, by the discharge of useful nutritional components and ions through urine by deterioration in the filtration function, leading to malnutrition and electrolyte loss, and the reduction in the kidneys of the produced amount of hematopoietic factor erythropoietin, renal anemia may result. As can be seen from the Japanese saying that that which is very important can be called "liver and kidneys" by lining up the first Japanese Kanji character of liver and kidneys, which are two organs for toxicant metabolism, the kidneys are a silent important organ.

The progression of renal function deterioration causes uremia, which causes symptoms such as nausea, grumpiness, fatigue, swelling, dizziness, hypertension, and breathing difficulty. When neglected, renal failure occurs and there is even death.

Regarding chronic kidney disease, although there are examples in which there is transition to chronic kidney disease by there being no recovery from acute renal failure caused by injury, shock or the like, it normally starts by renal function gradually deteriorating over a long period of time. Also, it is said that in many cases, chronic kidney disease involves kidney contraction, and once contracted, the kidneys will not recover.

In order to slow progression of the disease, primarily alimentotherapy and life control are performed, work is restricted in order to reduce stress, and proteins and salt are restricted in order to reduce strain on the kidneys. However, dietary restrictions over the long term place a large burden on patients.

Although drugs for directly treating chronic kidney disease are not known, the main drugs currently used from ameliorating chronic kidney disease are listed below.

1) Adrenocortical hormones, immunosuppressants
Used as symptomatic therapy for nephritis, nephrotic syndrome, and the like.

2) Antiplatelet drugs
Although used for the purpose of reducing the load on kidneys by improving blood flow, there is the risk that hemorrhaging will not stop.

3) Hypotensors (Ca antagonists, ACE inhibitors, ARB drugs, α-blockers)
Used for the purpose of reducing the load of kidneys by lowering blood pressure.

4) Calcium preparations, active vitamin D formulations
Used as a countermeasure for calcium deficiency at the time of renal function deterioration.

5) Iron preparations, erythropoietin
Used as a countermeasure for anemia at the time of renal function deterioration.

6) High uric acid therapeutic agents
Used as a countermeasure for high uric acid at the time of renal function deterioration.

7) Hyperlipidemia therapeutic agents
Reduces the load on kidneys by lowering serum cholesterol.

8) Diabetes therapeutic agents (sulfonyl-type, nateglinide-type, biguanide-type, insulin, and the like)
Used in the treatment of diabetes in diabetic renal disease.

All of these are for the purpose of delaying progression of the disease by symptomatic therapy or adjunctive therapy without directly improving renal function, and thus no fundamental pharmaceutical for chronic kidney disease presently exists.

Presently, fundamental treatment of renal function deterioration is limited to kidney transplantation or dialysis. However, kidney transplantations not only place a load on the patient, but there are also problems with the kidney donor. Also, dialysis heavily restricts the pattern of life since a patient is periodically restrained for a long period of time and treatment costs said to be 10,000,000 yen each year per patient are directly connected to the social problem of the national cost of medical care soaring.

Although urine tests measuring hematuria and the amount of proteins are adjunctively used for renal function, renal function is primarily determined using the serum creatinine value and the estimated glomerular filtration rate (eGFR) calculated by the following formula from the serum creatinine value and age.

Calculating formula estimating GFR (glomerular filtration rate)
Units: mL/min/1.73 m$^2$
Male: $eGFR=194 \times Cr^{-1.094} \times age^{-0.287}$
Female: eGFR=0.739×calculating formula for male eGFR When the above-mentioned eGFR becomes less than 90, it is determined as kidney disease, when it becomes less than 60, subjective symptoms such as swelling appear, when it becomes less than 30, dialysis preparation is necessary, and when it becomes less than 15, the possibility of death by uremia increases if kidney transplantation or dialysis is not performed. When suffering from chronic kidney disease, there is normally no improvement in the eGFR value and there is only delay in progression of the disease by abstinence and symptomatic therapy. In Japan, one person in every eight people is a chronic kidney disease patient and there is said to be 13,300,000 patients. There are presently 260,000 patients receiving dialysis and this is increasing yearly by 10,000 people. The development of therapeutic drugs for chronic kidney disease has become a national problem for saving the beleaguered medical economy let alone saving patients.

Also, it is known that chronic nephropathy causes anemia by reduction in the production of erythropoietin, which is a hematopoietic factor. Regarding the relationship between anemia and ALA, it has already been reported that ALA is effective in preventing anemia in piglets (for example, refer to Patent Document 1).

CITATION LIST

Patent Literature

Patent Document 1
 Japanese Patent No. 4754731

SUMMARY OF THE INVENTION

Problems to be Solved by the Invention

The object of the present invention is to provide an agent for ameliorating chronic kidney disease which is not an existing symptomatic therapeutic drug for chronic kidney disease, and which can increase the eGFR value and can improve renal function per se.

Means for Solving the Problems

The present inventors, in the continuation of much study regarding the application of ALA to medical treatment, when performing administration experimentation of radio-labeled ALA ($^{14}$C-ALA) for researching the pharmacokinetics of ALA, confirmed that accumulation of ALA-derived radiation was found in not only the anticipated liver and muscles, but also in the kidneys. Since the water-solubility of ALA is high, even if the amount of ALA-derived radiation is high in the kidneys, this is not questioned usually in particular. However, unexpectedly, it was found that when ALA is excessively administered, even if urine is discharged, radiation has remained in the kidneys even after the passing of time. From this, the idea that exogenously-administered ALA has remained in the kidneys, which thus means that it plays some role in the kidneys, was obtained.

Based on the above-mentioned idea, after much through analysis and examination of the relationship between ALA and ALA metabolites, and renal function, the present inventors reached the conclusion that it must be considered that, completely unexpectedly, ALA or ALA metabolites are largely involved in the function of filtering toxic substances of the kidneys.

Regarding the relationship between anemia and ALA, although it has already been reported that ALA is useful in the prevention of anemia in piglets as mentioned above, the causes are different even if the symptoms are the same for anemia associated with rapid growth of an individual and anemia associated with chronic kidney disease. Also, although we have found that ALA has an effect of ameliorating cancerous anemia, this is considered to be the control of cancer-specific hemolysis. Also, the present inventors have already found that ALA is useful in ameliorating diabetes. The amelioration of diabetes by ALA is considered to be primarily by improvement in the electron transfer system of mitochondria in muscles and the liver. Therefore, its mechanism is different from the mechanism for amelioration of chronic kidney disease by ALA. Although there are certainly many examples of chronic kidney disease progressing from diabetes, ALA improves the eGFR value of chronic kidney disease not from diabetes, and it is thus understood that the technical ideas are completely different for ameliorating diabetes and ameliorating chronic kidney disease by ALA.

Regarding the action of ALA in the amelioration of chronic kidney disease, it is assumed to be none of the already clarified various effects of ALA, effects as a porphyrin or a heme precursor, effect of improving the electron transfer system, effect of preventing hemolysis in cancer patients, immuno stimulating effect, and antioxidation effect. Although further research is necessary to explain the action mechanism of the amelioration of chronic kidney disease by ALA, from the eGFR value being directly improved and radiation derived from labeled ALA staying in the kidneys for a long time, it is deduced that it is valid to consider that ALA directly or ALA metabolites are involved in restoration of the basilar membrane involved in filtration by glomeruli in the kidneys and strengthening of the active filtration system. In chronic kidney disease, when renal function begins to deteriorate and there are filtration bodies having reduced filtration function, a load is placed on the remaining normal filtration bodies, resulting in the vicious cycle of the condition that the function of normal filtration bodies decreases. In the normal state, even if one of the kidneys is removed, there is available power in renal function in the normal case so as to lead a normal life. However, this available power gradually decreases before the start of chronic kidney disease and then the above-mentioned vicious cycle is entered. This available power portion is improved if a formulation including ALA is ingested before the start of chronic kidney disease, or the start of chronic kidney disease can be prevented or delayed by slowing such function deterioration. Furthermore, it was found that the effects of the present invention are increased by a metal-containing compound such as an iron compound being coordinated with ALA. When minerals are sufficient or when such are ingested separately, there are no problems with the administration of ALA alone. Among minerals, there is a tendency for iron to be insufficient in Japanese, whose amount of consumed red meat is small compared to other countries. For this reason, although iron is simultaneously added in the Examples for Japanese, it is not necessary when the target is a person having sufficient stored iron. Also, although it is widely known that ALA is metabolized to porphyrin and then shows PDT (photodynamic therapy) and PDD (photodynamic diagnosis) activity when exposed to light, light is not necessary for agent for ameliorating chronic kidney disease of the present invention.

The present inventors, after much further thorough study regarding administration methods, combination with other components and other agents, administration amounts, and the like, established an agent for ameliorating and/or preventing chronic kidney disease including ALA, thus leading to completion of the present invention.

That is, the present invention relates to
(1) an agent for ameliorating and/or preventing chronic kidney disease containing a compound represented by the following formula (I):

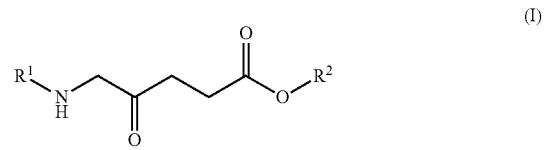

(wherein $R^1$ is a hydrogen atom or an acyl group, $R^2$ is a hydrogen atom, a linear or branched alkyl group, a cycloalkyl group, an aryl group, or an aralkyl group) or a salt thereof;

(2) the agent for ameliorating and/or preventing chronic kidney disease according to (1) above, wherein $R^1$ and $R^2$ are hydrogen atoms;
(3) the agent for ameliorating and/or preventing chronic kidney disease according to (1) or (2) above, further containing one or more metal-containing compounds;
(4) the agent for ameliorating and/or preventing chronic kidney disease according to (3) above, wherein the metal-containing compound is a compound containing iron, magnesium, zinc, nickel, vanadium, copper, chrome, molybdenum, or cobalt;
(5) the agent for ameliorating and/or preventing chronic kidney disease according to (3) above, wherein the metal-containing compound is a compound containing iron, magnesium, or zinc; and,
(6) the agent for ameliorating and/or preventing chronic kidney disease according to (3) above, wherein the metal-containing compound is a compound containing iron.

Also, the present invention relates to
(7) a method for improving and/or preventing chronic kidney disease, the method comprising: administering a compound represented by formula (I) or a salt thereof; or administering a compound represented by formula (I) or a salt thereof and a metal-containing compound. As a different embodiment, the present invention relates to a compound represented by formula (I) or a salt thereof, or a compound represented by formula (I) or a salt thereof and a metal-containing compound for use in a method for ameliorating and/or a method for preventing chronic kidney disease.

Effects of the Invention

By the agent for ameliorating and/or preventing chronic kidney disease of the present invention, it is possible to achieve superior amelioration of chronic kidney disease not in present drugs, namely, directly improve filtration capacity of kidneys and/or prevent decrease in filtration capacity of kidneys, and largely improve the quality of life of chronic kidney disease patients.

BRIEF DESCRIPTION OF THE DRAWINGS

FIG. 1 is a graph showing serum creatinine values and eGFR values before ingestion and after ingestion of the agent for ameliorating and/or preventing chronic kidney disease of the present invention.

DESCRIPTION OF EMBODIMENTS

In the present invention, chronic kidney disease means symptoms of chronic renal function deterioration generally called CKD in the medical field. It indicates renal function deterioration, excluding that which is transient, seen from either or both of:
(1) kidney damage following a structural or a functional abnormality;
(2) the state in which the glomerular filtration rate has decreased, and the cause of the onset of the disease is irrelevant.

Also, the effect of preventing chronic kidney disease of the present invention was confirmed by the effect diminishing when the ALA dosage was reduced and the original effect being achieved when the ALA dosage was restored.

As a compound used as the active ingredient in the agent for ameliorating and/or preventing chronic kidney disease of the present invention, a compound represented by formula (I) or a salt thereof (hereinafter, these are also collectively referred to as "ALAS") can be exemplified. ALA, also called δ-aminolevulinic acid, is when both $R^1$ and $R^2$ in formula (I) are hydrogen atoms, and is a type of an amino acid. As ALA derivatives, compounds other than ALA in which $R^1$ in formula (I) is a hydrogen atom or an acyl group and $R^2$ in formula (I) is a hydrogen atom, a linear or branched alkyl group, a cycloalkyl group, an aryl group, or an aralkyl group can be mentioned.

As the acyl group in formula (I), linear or branched alkanoyl groups having 1 to 8 carbon atoms such as formyl, acetyl, propionyl, butyryl, isobutyryl, valeryl, isovaleryl, pivaloyl, hexanoyl, octanoyl, and benzylcarbonyl; and aroyl groups having 7 to 14 carbon atoms such as benzoyl, 1-naphthoyl, and 2-naphthoyl groups can be mentioned.

As the alkyl group in formula (I), linear or branched alkyl groups having 1 to 8 carbon atoms such as methyl, ethyl, propyl, isopropyl, butyl, isobutyl, sec-butyl, tert-butyl, pentyl, isopentyl, neopentyl, hexyl, heptyl, and octyl groups can be mentioned.

As the cycloalkyl group in formula (I), cycloalkyl groups having 3 to 8 carbon atoms in which saturated or partially unsaturated bonds may be present such as cyclopropyl, cyclobutyl, cyclopentyl, cyclohexyl, cycloheptyl, cyclooctyl, cyclododecyl, and 1-cyclohexenyl groups can be mentioned.

As the aryl group in formula (I), aryl groups having 6 to 14 carbon atoms such as phenyl, naphthyl, anthryl, and phenanthryl groups can be mentioned.

As the aralkyl group in formula (I), the aryl portion can be the same as the above-mentioned aryl group examples and the alkyl portion can be the same as the above-mentioned alkyl group examples, and specifically, aralkyl groups having 7 to 15 carbon atoms such as benzyl, phenethyl, phenylpropyl, phenylbutyl, benzhydryl, trityl, naphthylmethyl, and naphthylethyl groups can be mentioned.

As the above-mentioned ALA derivative, a compound in which $R^1$ is formyl, acetyl, propionyl, or butyryl group, or the like, or a compound in which the above-mentioned $R^2$ is methyl, ethyl, propyl, butyl, or pentyl group, or the like is preferable; and a compound in which the combination of $R^1$ and $R^2$ is the combination of formyl and methyl, acetyl and methyl, propionyl and methyl, butyryl and methyl, formyl and ethyl, acetyl and ethyl, propionyl and ethyl, or butyryl and ethyl, or the like can be preferably mentioned.

For the ALAs, it is sufficient that they act as an active ingredient in vivo in the state of an ALA represented by formula (I) or a derivative thereof and it is sufficient that, according to the form of administration, they can be administered as various salts, esters, or prodrugs (precursors) decomposed by enzymes in the body, in order to enhance the solubility thereof. For example, as salts of ALA and a derivative thereof, pharmaceutically acceptable acid addition salts, metal salts, ammonium salts, organic amine addition salts, and the like can be mentioned. As the acid addition salts, various inorganic acid salts such as hydrochlorides, hydrobromates, hydroiodides, phosphates, nitrates, and sulfates; and various organic acid addition salts such as formates, acetates, propionates, toluenesulfonates, succinates, oxalates, lactates, tartrates, glycolates, methanesulfonates, butyrates, valerates, citrates, fumarates, maleates, and malates for example can be exemplified. As metal salts, various alkali metal salts such as lithium salts, sodium salts, and potassium salts; various alkali earth metal salts such as magnesium salts and calcium salts; and various metal salts such as those of aluminum and zinc can be exemplified. As ammonium salts, ammonium salts and alkyl ammonium salts such as tetramethyl ammonium salts can be exemplified. As organic amine salts, various salts such as triethyl amine salts, piperidine salts, morpholine salts, and toluidine salts can be exemplified. These salts may be used as a solution at the time of use.

Among the above-mentioned ALAs, ALA, various esters such as ALA methylester, ALA ethylester, ALA propylester, ALA butylester, and ALA pentylester, and hydrochlorides, phosphates and sulfates of these ALA esters are preferable, and ALA hydrochloride and ALA phosphate can be exemplified as particularly preferable.

The above-mentioned ALAs can be produced by any well-known method of chemical synthesis, production by microorganisms, and production by enzymes. Also, the above-mentioned ALAs may be in the form of a hydrate or a solvate and also, they may be used alone or by appropriately combining two or more thereof.

The agent for ameliorating and/or preventing chronic kidney disease of the present invention preferably further contains a metal-containing compound in a range that does not cause excess symptoms. As the metal portion of such a metal-containing compound, iron, magnesium, zinc, nickel, vanadium, cobalt, copper, chrome, and molybdenum can be mentioned. Iron, magnesium, and zinc are preferable, and among these, iron can be preferably exemplified.

The above-mentioned iron compound may be an organic salt or an inorganic salt. As inorganic salts, ferric chloride, iron sesquioxide, iron sulfate, and ferrous pyrophosphate can be mentioned. As organic salts, organic acid salts such as carboxylates, for example, citrates such as ferrous citrate, sodium iron citrate, sodium ferrous citrate, and ammonium iron citrate, which are hydroxycarboxylates, ferric pyrophosphate, iron lactate, ferrous gluconate, sodium iron diethylenetriaminepentaacetate, ammonium iron diethylenetriaminepentaacetate, sodium iron ethylenediaminetetraacetate, ammonium iron ethylenediaminepentaacetate, sodium iron dicarboxymethylglutamate, ammonium iron dicarboxymethylglutamate, ferrous fumarate, iron acetate, iron oxalate, ferrous succinate, and sodium iron succinate citrate, and heme iron, iron dextran, iron triethylenetetramine, lactoferrin iron, transferrin iron, sodium iron chlorophyllin, ferritin iron, saccharated iron oxide, and ferrous glycine sulphate can be mentioned.

As the above-mentioned magnesium compound, magnesium citrate, magnesium benzoate, magnesium acetate, magnesium oxide, magnesium chloride, magnesium hydroxide, magnesium carbonate, magnesium sulfate, magnesium silicate, magnesium nitrate, diammonium magnesium diethylenetriaminepentaacetate, disodium magnesium ethylenediaminetetraacetate, and magnesium protoporphyrin can be mentioned.

As the above-mentioned zinc compound, zinc chloride, zinc oxide, zinc nitrate, zinc carbonate, zinc sulfate, diammonium zinc diethylenetriaminepentaacetate, disodium zinc ethylenediaminetetraacetate, zinc protoporphyrin, and zinc-containing yeast can be mentioned.

The above-mentioned metal-containing compounds can be used alone, or by combining two or more thereof. The dosage of the metal-containing compound may be 0 to 100 times the administered amount of ALA in molar ratio, and preferably 0.01 to 10 times, and more preferably 0.1 to 8 times.

The ALAs and the metal-containing compound contained in the agent for ameliorating and/or preventing chronic kidney disease of the present invention can be administered as a composition containing the ALAs and the metal-containing compound or each separately. When each is separately administered, it is preferable that they are administered simultaneously. Herein, simultaneously means not only performed at the same time, but also performed, if not at the same time, without a considerable space between both so as administration of the ALAs and the metal-containing compound can achieve additive effects and preferably synergistic effects.

As the administration route of the agent for ameliorating and/or preventing chronic kidney disease of the present invention, oral administration, also including sublingual administration; or parenteral administration such as direct administration to the kidneys by a catheter; inhalation administration, intravenous administration, also including an intravenous drip, transdermal administration by a cataplasm, a suppository, or administration by forced enteral nutrition using a nasogastric tube, a nasointestinal tube, a gastrostomy tube, or an enterostomy tube, or the like can be mentioned.

As the dosage form of the agent for ameliorating and/or preventing chronic kidney disease of the present invention, although such can be appropriately determined according to the above-mentioned administration route, parenteral solutions, drops, tablets, capsules, fine granules, powder medicines, liquid formulations, liquid agents dissolved in a syrup or the like, cataplasms, and suppositories can be mentioned.

In order to prepare the agent for ameliorating and/or preventing chronic kidney disease of the present invention, a pharmaceutically acceptable carrier, excipient, diluent, additive, disintegrant, binder, covering agent, lubricant, glidant, lubricating agent, flavoring agent, sweetener, solubilizer, solvent, gelling agent, and/or nutritional supplement can be added according to necessity. Specifically, water, normal saline solution, animal fats and oils, plant oils, lactose, starch, gelatin, crystalline cellulose, gum, talc, magnesium stearate, hydroxypropylcellulose, polyalkylene glycol, polyvinyl alcohol, and glycerin can be exemplified. When preparing the agent for ameliorating and/or preventing chronic kidney disease of the present invention as an aqueous solution, in order to prevent degradation of the ALAs, it is necessary to take care so that the aqueous solution does not become alkaline. When the aqueous solution becomes alkaline, degradation can be prevented by removing oxygen.

As the amount, frequency, and period of administration of the agent for ameliorating chronic kidney disease of the present invention, although such differ by the age, weight, symptoms, and the like of the chronic kidney disease patient, based on ALA molar conversion, 0.01 mmol to 25 mmol/day, preferably 0.025 mmol to 7.5 mmol/day, more preferably 0.075 mmol to 5.5 mmol/day, and further preferably 0.2 mmol to 2 mmol/day can be given as the administration amount of ALAs for one adult. As the frequency of administration, administration one to several times per day or continuous administration by an intravenous drip or the like can be exemplified. As the administration period, this can be determined by a known method by a pharmacologist or a clinician in the relevant technical field based on indicators showing renal function such as creatinine, urea nitrogen, and eGFR. Also, as the amount, frequency, and period of administration of the agent for preventing chronic kidney disease of the present invention, although such differ by the age, weight, symptoms, and the like of the subject, based on ALA molar conversion, 0.004 mmol to 6.5 mmol/day, preferably 0.008 mmol to 2 mmol/day, more preferably 0.15 mmol to 1.5 mmol/day and further preferably 0.17 mmol to 0.45 mmol/day can be given as the administration amount of ALAs for one adult. As the frequency of administration, administration one to several times per day can be exemplified. As the administration period, this can be determined by a known method by a pharmacologist or a clinician in the relevant technical field based on indicators showing renal function such as creatinine, urea nitrogen, and eGFR while observing so that deterioration in renal function does not occur.

Below, the present invention is more specifically explained by the Examples, but the technical scope of the present invention is not limited to these illustrations.

EXAMPLES

Example 1

A 72 year-old woman suffering long-term from chronic kidney disease was examined. This woman has not been diagnosed with diabetes. Urea nitrogen, serum creatinine, eGFR, and the diagnosis of chronic kidney disease on (1) Dec. 22, 2010 and on (2) Feb. 24, 2011 after ingesting 50 mg of aminolevulinic acid phosphate and 57.4 mg of sodium ferrous citrate each day for about seven weeks from Jan. 4, 2011 are shown in Table 1 below.

TABLE 1

|  | Urea nitrogen (mg/dL) | Serum creatinine (mg/dL) | eGFR (mL/min/1.73 m$^2$) | Diagnosis |
|---|---|---|---|---|
| 2010/12/22 | 47.00 | 2.77 | 13.80 | Fifth stage (renal failure) |
| 2011/02/24 | 37.00 | 2.37 | 16.70 | Fourth stage |

As is clear from Table 1 above, chronic kidney disease has improved. Examples of a person once diagnosed as renal failure improving are rare, and thus it is understood that the effects of the agent for ameliorating chronic kidney disease of the present invention are distinctive.

Example 2

The effects of ingesting aminolevulinic acid phosphate and sodium ferrous citrate were examined for a man diagnosed with chronic kidney disease. From about the age of 42, this man's serum creatinine rose to about 1.3 and although he has been prescribed Uralyt (Nippon Chemiphar Co., Ltd.), he has not been diagnosed with diabetes.

The results of the examination values arranged in chronological order for:

(a) before starting to ingest aminolevulinic acid phosphate and sodium ferrous citrate;
(b) after one month of ingesting 50 mg of aminolevulinic acid phosphate and 57.4 mg of sodium ferrous citrate;
(c) after one month of switching to ingesting 5 mg of aminolevulinic acid phosphate and 5.74 mg of sodium ferrous citrate thereafter;
(d) after two months of switching to ingesting 5 mg of aminolevulinic acid phosphate and 5.74 mg of sodium ferrous citrate; and
(e) after one month of returning to ingesting 50 mg of aminolevulinic acid phosphate and 57.4 mg of sodium ferrous citrate thereafter are shown below in Table 2, respectively.

TABLE 2

|  | Urea nitrogen (mg/dL) | Serum creatinine (mg/dL) | eGFR (mL/min/1.73 m$^2$) |
|---|---|---|---|
| a | 15.60 | 1.38 | 40.60 |
| b | 14.00 | 1.21 | 46.90 |
| c | 12.90 | 1.14 | 50.10 |
| d | 14.10 | 1.25 | 45.30 |
| e | 13.10 | 1.16 | 49.77 |

As is clear from Table 2 above, when 50 mg of aminolevulinic acid phosphate was ingested, the eGFR value remarkably improved (increased) and although the improvement rate of the eGFR value was lowered when reduced to 5 mg of aminolevulinic acid phosphate and 5.74 mg of sodium ferrous citrate, remarkable improvement was seen when once again returned to 50 mg. The man who ingested was relieved from the fatigue peculiar to chronic kidney disease and improved to the extent that he was able to enjoy walking for about 30 minutes two or three times a week. It is thus understood that the quality of life can be remarkably improved by the agent for ameliorating chronic kidney disease of the present invention.

Example 3

The effects of ingesting aminolevulinic acid phosphate and sodium ferrous citrate were examined for a 74 year-old man diagnosed with chronic kidney disease after removing one of his kidneys about 5 years ago because of cancer. This male had an HbA1c of 6.6 and was diagnosed as not having diabetes. FIG. 1 shows the serum creatinine values and the eGFR values before ingestion and after ingestion of 150 mg of aminolevulinic acid phosphate and 172 mg sodium ferrous citrate per day.

As is clear from FIG. 1, remarkable reduction in serum creatinine is shown and thus it is eloquently shown that ALA is useful for chronic kidney disease. In the case of this patient, although he became to suffer from chronic kidney disease by the physical aspects as the removal of one of his kidneys, that there were also effects for this kind of patient means that the capacity of the filtration membrane of the kidney per unit area improved and there is thus interest in examining the action mechanism of the agent of the present invention.

INDUSTRIAL APPLICABILITY

The agent for ameliorating and/or preventing chronic kidney disease of the present invention can be advantageously utilized in the medical field.

The invention claimed is:
1. A method for ameliorating and/or preventing chronic kidney disease comprising: administering to a subject with chronic kidney disease an agent comprising a compound represented by the following formula (I):

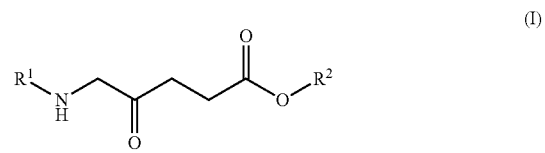

wherein R¹ is a hydrogen atom or an acyl group; and R² is a hydrogen atom, a linear alkyl group, a cycloalkyl group, an aryl group, or an aralkyl group, or a salt thereof.

2. The method according to claim wherein 1, and R¹ and R² are hydrogen atoms.

3. The method according to claim 1, wherein the agent further comprises one or more metal-containing compounds.

4. The method according to claim 3, wherein the metal-containing compound is a compound containing iron, magnesium, zinc, nickel, vanadium, copper, chrome, molybdenum, or cobalt.

5. The method according to claim 3, wherein the metal-containing compound is a compound containing iron, magnesium, or zinc.

6. The method according to claim 3, wherein the metal-containing compound is a compound containing iron.

7. The method according to claim 2, wherein the agent furrther comprises one or more metal-containing compounds.

8. The method according to claim 7, wherein the metal containing compound is a compound containing iron, magnesium, zinc nickel, vanadium, copper, chrome, molybdenum, or cobalt.

9. The method according to claim 7, wherein the one or more metal-containing compound is a compound containing iron, magnesium, or zinc.

10. The method according to claim 7, wherein the one or more metal-containing compound is a compound containing iron.

* * * * *